(12) United States Patent
Norris

(10) Patent No.: US 6,825,619 B2
(45) Date of Patent: Nov. 30, 2004

(54) FEEDBACK-CONTROLLED LED SWITCHING

(75) Inventor: Mark A. Norris, Boulder, CO (US)

(73) Assignee: Datex-Ohmeda, Inc., Madison, WI (US)

(*) Notice: Subject to any disclaimer, the term of this patent is extended or adjusted under 35 U.S.C. 154(b) by 0 days.

(21) Appl. No.: 10/215,878

(22) Filed: Aug. 8, 2002

(65) Prior Publication Data

US 2004/0030229 A1 Feb. 12, 2004

(51) Int. Cl.[7] .............................................. H05B 37/02
(52) U.S. Cl. ....................... 315/149; 315/291; 315/307; 356/41; 372/38.02; 600/310; 600/323
(58) Field of Search ................................ 315/149, 151, 315/291, 307; 600/323, 310; 356/41; 372/38.02, 38.07

(56) References Cited

U.S. PATENT DOCUMENTS

| | | | | |
|---|---|---|---|---|
| 4,001,667 A | * | 1/1977 | Bober | ........................ 356/41 |
| 4,504,776 A | * | 3/1985 | Haville | ........................ 323/288 |
| 5,099,139 A | * | 3/1992 | Nishimura | ................... 327/103 |
| 6,097,159 A | * | 8/2000 | Mogi et al. | .................. 315/149 |

* cited by examiner

Primary Examiner—Wilson Lee
Assistant Examiner—Ephrem Alemu
(74) Attorney, Agent, or Firm—Marsh Fischmann & Breyfogle LLP

(57) ABSTRACT

An oximeter has an op-amp with a first input, a second input, and an output, the first input being directly connected to a reference voltage. A switch has an input connected to the output of the op-amp, and has a plurality of switch outputs. A transistor has a control input connected to one of the plurality of outputs, and has a current source terminal and a supply terminal. A diode is connected to the current source terminal of the transistor. The supply terminal of the transistor is connected both to the second input of the op-amp and to a second one of the plurality of switch outputs. The switch is thereby in a feedback loop of the op-amp, effecting a feedback-controlled switch for switching the diode on and off.

31 Claims, 3 Drawing Sheets

FEEDBACK-CONTROLLED LED SWITCHING

CROSS REFERENCE TO RELATED APPLICATIONS

This application is related to U.S. patent application Ser. No. 10/215,908 titled "Ferrite Stabilized LED Drive", and to U.S. patent application Ser. No. 10/215,935 titled "Oximeter With Nulled O-Amp Current Feedback" both filed on Aug. 8, 2002.

BACKGROUND

1. Field of the Invention

The present invention relates generally to feedback-controlled switching and, more particularly, to pulse oximetry having feedback-controlled LED switching where noise in a sense current and in LED drive current are reduced by switching a reference voltage in the feedback loop of an op-amp circuit.

2. Related Work

A pulse oximeter is a type of blood gas monitor which non-invasively measures an amount of saturation of oxygen in the blood. The saturation of oxygenated blood may be determined from the differentiated absorption for two plethysmographic waveforms measured at separate wavelengths. The two waveforms are typically produced by driving a visible red light-emitting diode (LED) and an infra-red LED to produce two lights that pass through a patient's tissue, and then detecting the light on the same or an opposite side of the tissue using one or more photodetectors. Although most conventional oximeters use the red and infra-red LEDs, other devices such as surface emitting laser devices having different wavelengths may also be used, and the number of LEDs can vary according to the specific measurement application. For example, it is known to set a number of laser diodes to be equal to or greater than the number of blood analytes that are to be measured by an instrument The two LEDs emit light at different wavelengths. The photodetector output signal indicates the attenuation of the two different wavelength lights after the lights pass through the patient's body. In order to obtain a degree of consistency and ease of use, the photodetector is generally placed in a clip or similar device attached to the patient's finger or earlobe. Attenuation of the lights is substantially constant except for the flow of blood. Thus, the constant attenuation due to the light passing through the patient's skin and other tissue can be determined and filtered from the photodetector signal, thereby obtaining a signal representing the desired blood oxygen characteristics. Signals containing a component related to a patient's pulse are known as plethysmographic waves and are used in blood gas saturation measurements. So, for example, the red/infrared ratio for waveforms at different wavelengths may be analyzed to obtain oxygenization values.

It is known to activate the red and infra-red LEDs during different time periods, where the two LEDs are cycled on and off alternately, in order to enable the photodetector to receive one signal at a time. As a result of generating LED pulse trains in a time-division manner, a composite time-division signal is then received by the photodetector. Alternatively, switching of LEDs may be related to other parameters such as maintaining a particular duty cycle without regard to time-division multiplexing (TDM). Various methods, not limited to TDM or to periodic switching, for modulating the LEDs can also be employed.

In order to increase the accuracy and resolution of the oximeter, it is desirable to reduce noise in the circuitry used to produce one or more drive currents for causing the LEDs to illuminate. Conventional LED drive circuits have been designed to minimize photic noise generated by the LEDs, in order to maximize a signal-to-noise ratio for the arterial attenuation signal(s) used in processing oximetry data. However, as is further discussed below, conventional LED driving circuits do not consider that a switching of a reference voltage may be a source of noise.

A typical apparatus employing a time-division diode driving scheme includes LED current drivers having a serial configuration where the outputs of two voltage-to-current converters are switched so that only one of two LEDs, connected in a back-to-back configuration, is on at any given time. The LED drive circuitry activates the red LED for a quarter cycle and activates the infra-red LED for a quarter cycle, with a quarter cycle "dark" period separating each successive activation period. Since the two LEDs are on only periodically, less noise is generated from the LEDs and corresponding LED drive circuitry. This conventional LED drive circuitry uses ganged-type switch banks to alternately switch on/off both the input and the output of each voltage-to-current converter, thereby reducing noise from both the switching and voltage-to-current conversion circuitry. Both the reference voltage input and the resultant drive current output of a conventional dual LED drive circuit are simultaneously switched off because merely setting the reference set point to zero does not account for offset voltages in the op-amp that keep the op-amp in a "turned-on" state and that keeps the LED drive current turned on. The LEDs are thus driven to provide light transmission with digital modulation at a fixed low frequency f, where each period 1/f contains the aforementioned four quarter-cycle periods.

As shown in FIG. 3, a conventional LED drive circuit includes a reference voltage source 324 that generates an analog output, which is fed to a digital-to-analog (D/A) converter 325. The output of the D/A 325 is then output to a switch bank 326. When the switch bank 326 is in an ON condition, the D/A output signal is switchably connected to one of two voltage-to-current (V/I) converters 328, 329. When the switch bank 326 is in an OFF condition, the D/A output signal is switchably connected to the other of the two V/I converters 328, 329. The output of the currently activated V/I 328, 329 is connected to a pair of back-to-back LEDs 301, 302 via a second switch bank 327, which disconnects the output of the currently deactivated V/I converter 328, 329 from the LEDs 301, 302.

A conventional LED drive circuit, such as that described above, switches the reference voltage to each V/I converter. This conventional switching of the reference voltage creates a noise that is then amplified by the respective V/I converter. Although the conventional switching described above disables both the input and output of serially-oriented LED drivers, resulting in less overall average LED drive circuitry noise, it does not consider the noise created by the switching itself.

Oximetry noise is known to those of ordinary skill in the oximetry art to include any signal portions relating to ambient light, motion artifacts, absorption variance other than the plethysmographic effects of interest, electromagnetic radiation, electrical interference, magnetic fields, electronic interference such as harmonics or RF, and others.

Conventional voltage reference sources are chosen for use as a low noise DC voltage reference for a digital to analog conversion circuit 325. In that regard, the conventional voltage reference of FIG. 3 has a lowpass output filter (not shown) with a low corner frequency of 1 Hz. The digital to analog converter 325 also has a lowpass filter at its output with a similar low corner frequency of 1 Hz. The digital to analog converter 325 provides signals for each of the emitters 301, 302.

In the conventional FIG. 3 circuit, voltage to current converters 328, 329 can each have a feedback loop (not shown) that is configured to have a low pass filter to reduce noise. The low pass filtering function of the voltage to current converter 328, 329 has a corner frequency of just above 625 Hz, which is the switching speed for the emitters 301, 302.

Other filters (not shown) are typically used to reduce the effects of ambient electromagnetic noise in electronic monitoring instruments, especially when the noise source frequency (or a harmonic of the noise source frequency) is approximately the same as the fundamental frequency or harmonics at which the instrument is operating. In addition, a static filtering using a bandpass filter has been conventionally used to remove a portion of the photodetector's output noise signal that is outside an identified bandwidth of interest, leaving random and/or erratic noise that is within the filter's passband. A processor has conventionally been used to separate-out primary signal portions in order to isolate and identify the remaining noise signals, which are then removed using, for example, an adaptive noise canceller. Such a scheme is known as correlation canceling.

What is needed is a lower noise diode driving circuit, where a lower frequency low-pass filtering may be employed. An improved method in an oximeter for switching a diode current source reference voltage is needed, in order to eliminate noise caused by the switching itself.

SUMMARY OF THE INVENTION

The present inventor has recognized that noise due to an LED driving circuit can create cognizable artifact, particularly when oversampling type processing is used in oximetry systems. Switching noise in an LED current drive was conventionally not considered by designers of oximetry systems because typical processing systems were unable to "see" this switching noise being produced by a diode current driving circuit. The present invention uniquely maintains an ultra-low noise by eliminating a switching of a reference voltage being provided to an LED driving circuit.

In general, none of the prior art has considered the significance of noise in an oximetry system due to a diode current driving circuit. In particular, conventional assumptions regarding oximetry noise did not consider switching noise of an LED drive circuit, either because processing was unable to discern or distinguish noises as being due to the diode driving circuit, or simply because it was assumed that such noise could simply be filtered-out as estimated noise components when processing a detected signal. In addition, conventional oximetry systems have not attempted to provide a "clean" LED drive circuit with expanded dynamic range. With state-of-the-art processing hardware and software, e.g., oversampling, a higher processing capability and greater resolution allows "seeing" smaller noises that were previously unnoticed. Along with improving resolution, it is of paramount importance to reduce noise sources in the LED drive circuitry of an oximeter rather than separating-out resultant signals during processing of signals from the oximeter's photodetector. By using as clean a diode driving circuit as possible, less noise is present in downstream signals, and dynamic performance is improved, especially at low frequencies.

In order to improve over conventional LED drive systems, the present invention includes an apparatus and method for switching of one or more LEDs. The apparatus contains a switch, which turns the LEDs on and off, in the feedback loop of an op-amp driver circuit. This arrangement allows the current set point reference voltage to be directly connected to the op-amp, which reduces the noise of the LED drive circuit. A variation of the apparatus includes a variable resistance used as the current sensing resistor of the LED drive circuit.

A method according to the present invention includes placing a switch in the feedback loop of an op-amp LED driver circuit, and utilizing the switch for on/off switching a reference voltage to the op-amp in order to lower a noise current of the LED driver circuit. A variation of the method further includes changing the resistance of a current-sensing resistor to vary LED drive currents.

The present invention can be applied to any number of diodes being driven by a feedback type amplifier, so that a reference voltage is not switched but is directly applied to the amplifier, which has a switch in its feedback loop that controls the on/off switching of the diodes.

This summary does not limit the invention, which is instead defined by the appended claims.

BRIEF DESCRIPTION OF THE DRAWING FIGURES

The above and other objects and advantages of the present invention will become more apparent by describing in detail preferred embodiments thereof with reference to the accompanying drawing figures in which.

DETAILED DESCRIPTION OF THE PREFERRED EMBODIMENTS

Figure 4:
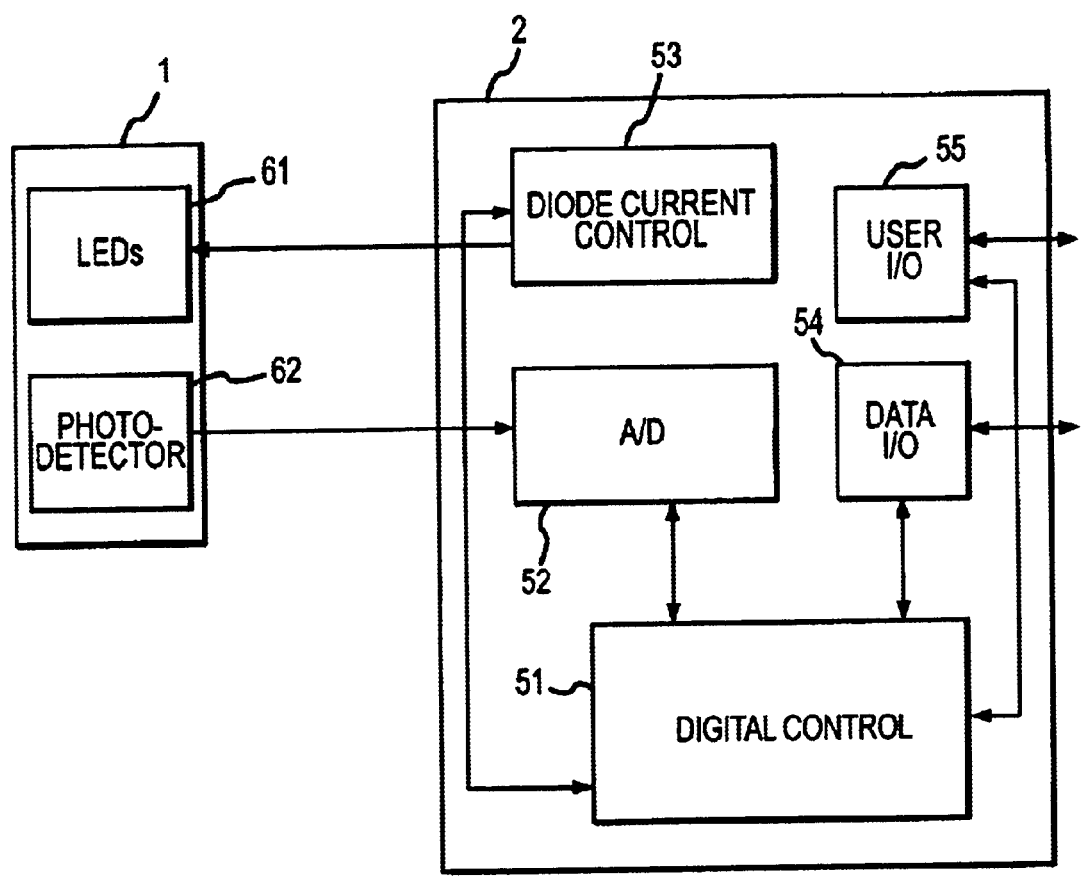
FIG. 4 is a highly schematic diagram of a conventional pulse oximeter system.

FIG. 4 shows the basic elements of an exemplary pulse oximeter used for implementing the disclosed embodiments. A probe 1 is affixed to a patient to be monitored. The probe 1 contains LEDs 61 that illuminate when a current passes through them, and a photodetector 62 for detecting light. The light emitted by the LEDs 61 passes through the patient's tissue and a portion of the emitted light is detected by at least one photodetector 62 that is placed on a same or a different location on the patient. The detected light can, therefore, be in a direct path of the emitted light, or can detect reflected light. A monitor 2 contains a user input/output section 55 that may include a speaker, keypad, and display device which allow a user to operate the pulse oximeter. For example, a user is able to adjust a measurement period and/or measurement cycle parameters, and see and hear measurement data and operational status. A digital control section 51 controls the internal operations of the oximeter. A diode current driver circuit 53 controls a current being supplied to individual LEDs 61. An analog-to-digital (A/D) converter 52 receives detection signals from the photodetector 62, converts those detected signals to digital signals that are then processed by the digital control section 51. The monitor 2 also contains a data input/output section 54 that provides both a serial digital data output and an analog output, which allow the oximeter to interface with external equipment, such as a computer. The data input/output section 54 also accepts control signals from external equipment in order to remotely change or control operation of the oximeter.

Figure 1:
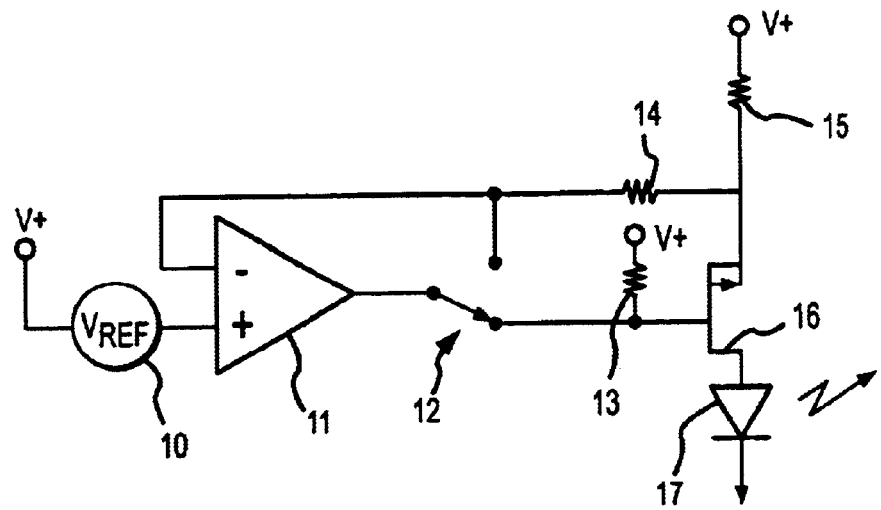
FIG. 1 is a circuit diagram of an op-amp type LED drive circuit and an LED used in an oximeter, according to a first embodiment of the present invention.

A first embodiment of the invention will now be described with reference to FIG. 1. FIG. 1 is a circuit diagram of an op-amp type LED drive circuit and an LED used in an oximeter. An op-amp 11 has an inverting input (−), a non-inverting input (+), and an output terminal. The output terminal of the op-amp 11 is connected to the input (common terminal) of a switch 12. The switch 12 has multiple switch outputs that can be individually connected to the common terminal of the switch 12.

A reference voltage source 10 is connected between a supply voltage $V_{DD}$ and the non-inverting terminal of the op-amp 11. As will be further discussed below, it is preferable to connect the reference voltage directly to the non-inverting input of the op-amp 11. The inverting terminal of the op-amp 11 is connected to a first output of the switch 12 and to one end of a feedback resistor 14. The other end of the feedback resistor 14 is connected to one end of a current sensing resistor 15 and to the source of a PMOS FET 16. The other end of the current sensing resistor 15 is connected to the supply voltage $V_{DD}$. The gate of the PMOS FET 16 is connected to a second output of the switch 12 and to one end of a pull-up resistor 13. The other end of the pull-up resistor 13 is connected to the supply voltage $V_{DD}$. The drain of the PMOS FET 16 is connected to the anode of a diode 17, which is either a red light emitting diode (LED) or an infrared diode. The cathode of the diode 17 is connected to ground potential.

In the embodiment of FIG. 1, the two outputs of switch 12 are labeled as "ON" and "OFF." When the switch 12 is in the ON position, the op-amp 111 drives the PMOS FET 16 using feedback from current sensing resistor 15 through feedback resistor 14, in order to control a regulation of current passing through the diode 17. When the switch 12 is in the OFF position, the op-amp 11 output follows the reference voltage from reference voltage source 10, and the pull-up resistor 13 holds the PMOS FET 16 in an off state.

The current sensing resistor 15 is chosen so that a nominal current flowing through the resistor 15 corresponds to, or matches, a current set point of the op-amp 11 that is set by the reference voltage being input to the non-inverting input of the op-amp 11. By feeding back the diode current value sensed by current sensing resistor 15 to the inverting input of op-amp 11, the op-amp 11 equalizes-out any variation in current by amplifying the variation as an inverted signal, thereby causing a subtraction of the variation. By using the reference voltage to control the current setpoint, the drive current to the diode 17 is maintained with a desired regulation.

According to the present invention, the reference voltage is kept fixed as an ultra-low-noise voltage source that is directly connected to the non-inverting input of the op-amp 11. The reference voltage source 10 is therefore not switched at all, so that no switching noise is generated. The constant feedback set point that is not turned on or off results in a stable circuit that can be effectively low-pass filtered, therefore resulting in a much quieter operation compared with conventional LED drive circuits.

There are two general types of noise associated with an op-amp that are relevant, "1/f noise" that is noise which becomes greater per unit bandwidth as the frequency decreases, and "white noise" that remains constant and flat over a broad range of frequencies. The low-frequency noise is of particular interest in the reference voltage of an op-amp used in oximetry applications. Reference voltages always have some inherent noise, and by being more adaptable to low-pass filtering, the reference voltage is made less noisy. As a result of the present invention where the reference voltage is not switched, a reference voltage source can be used that has a very low bandwidth, and an extremely large amount of low-pass filtering that eliminates all low-frequency noise effects, including harmonics of corresponding low-frequency noise (e.g., eliminating any effects from a patient heartbeat, even below 30 beats per minute (0.5 Hz) and above 250 beats per minute). In order to have as little noise as possible in a frequency band of interest, by not switching the reference, the bandwidth of the reference can be very low (e.g., 0.02 to 0.003 Hz). Potential interfering signals within the LED driver circuit from, for example, harmonics of a heartbeat, Meyer waves, and respiration-related noises are greatly reduced. As a result of direct connection of the reference voltage source 10 to the op-amp 11, the low-pass filtering removes any noise on the constant reference voltage because the requirements for a reference voltage source (e.g., bandwidth) are much less than with conventional devices. By not directly switching the reference voltage, the reference voltage signal is much cleaner compared with conventional diode driving circuits. By placing the respective switch for a diode within the feedback portion of the driving circuit, any noise being injected by the switch is driven out by the op-amp's feedback loop. In other words, an op-amp cannot get rid of noise from a reference voltage being applied to its non-inverting input, whereas by changing the generation location for a switching of the reference voltage to be within the feedback loop of the op-amp, the switching noise is driven out by the cancellation action of the feedback.

One embodiment of the oximeter modulates the switching of the diodes using code-division multiple access (CDMA) ("spread spectrum") methods, or similar modulation scheme. In CDMA, the modulation encodes the signal being transmitted by the diode 17 using a pseudo-random sequence which a receiver can use to decode a received signal. Each different random sequence can correspond to a different diode channel. Thus, for this CDM application, the diode switching relates to a non-periodic diode drive signal. The above-discussed frequency bandwidth of the reference voltage is meant to be well below the demodulated signal (e.g., physiological waveforms of 0.5 to 4.5 Hz), whereas the op-amp is driving the LEDs at a much higher frequency (e.g., from about 200 Hz to several kHz).

Figure 2:
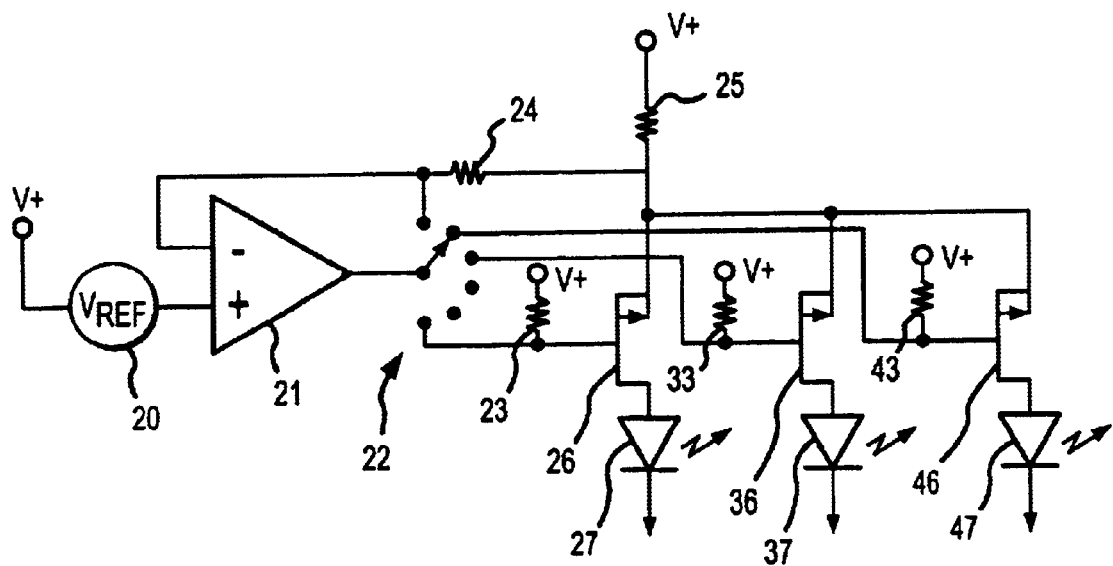
FIG. 2 is a circuit diagram of an op-amp type LED drive circuit and LEDs used in an oximeter, according to a second embodiment of the present invention.
Figure 3:
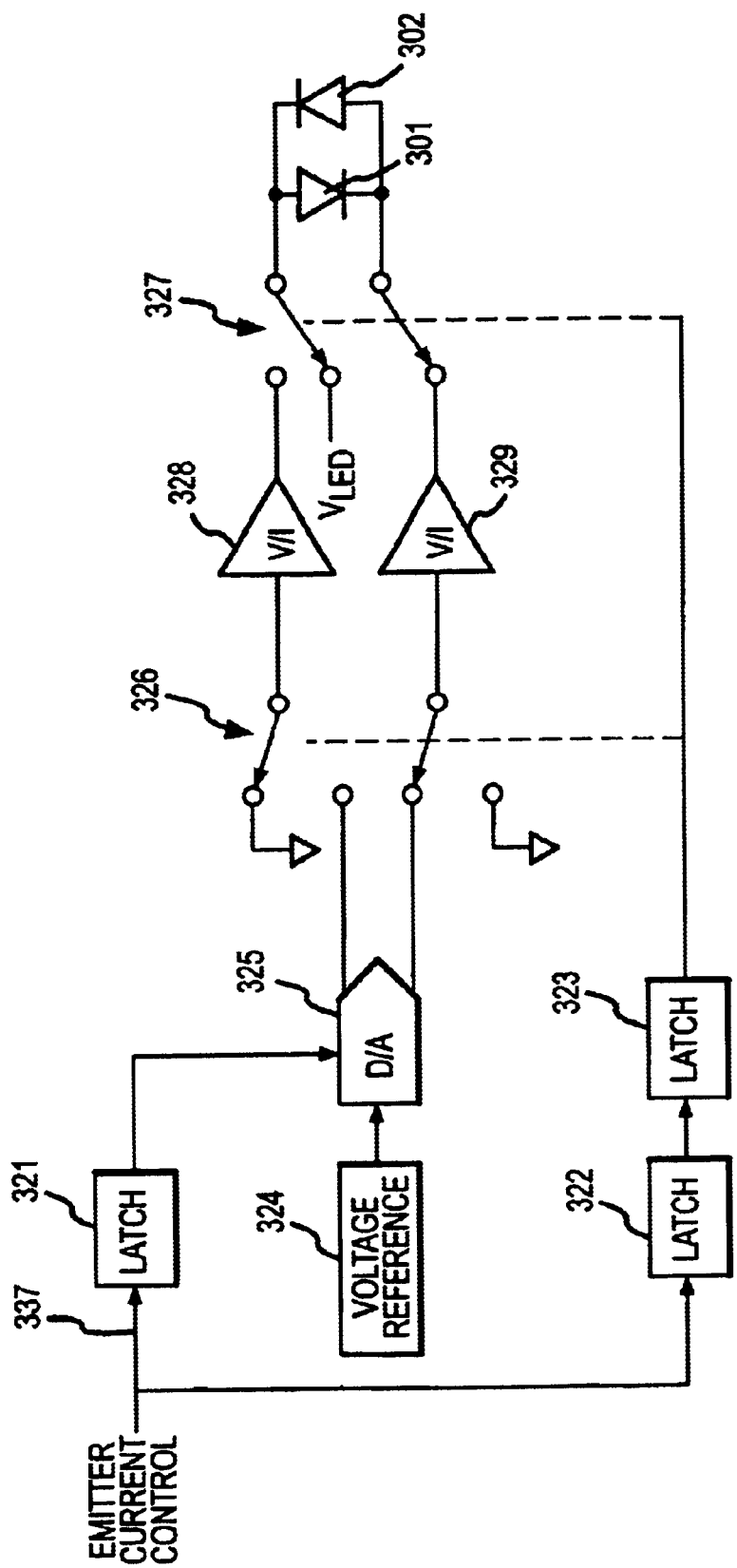
FIG. 3 illustrates a conventional LED driving circuit that switches a reference voltage being supplied to a voltage-to-current converter.

A second embodiment of the invention will now be described with reference to FIG. 2. FIG. 2 is a circuit diagram of an op-amp type LED drive circuit used in an oximeter having a plurality of diodes. Diodes 27, 37, 47 are switched on or off in a manner where only one diode is activated at any given time. The FIG. 2 configuration differs from the FIG. 1 circuit in that a switch 22 has more than two outputs. The number of outputs of the switch 22 is greater than or equal to the number of diodes to be switched. Each one of the diodes 27, 37, 47 has its anode connected to the source of a corresponding PMOS FET 26, 36, 46. Each drain of PMOS FETs 26, 36, 46 is connected to a common point that connects one end of the current sense resistor 25 and the feedback resistor 24. Each gate of each respective PMOS FET 26, 36, 46 is connected to a separate output of switch 22. Otherwise, the FIG. 2 circuit is basically the same as the FIG. 1 circuit. The FIG. 2 circuit thus extends the FIG. 1 circuit to control several current sources. The limit of only being able to turn one of the diodes 26, 36, 46 on at any given time is not a problem in oximetry, which typically does not require that multiple LEDs be on at one time.

A variation of the FIG. 1 and FIG. 2 circuits includes changing the value of the current sensing resistor 15, 25 for providing varying LED drive currents. In such a circuit, the current sensing resistor 15, 25 is implemented by using a network of resistors (not shown) that is adapted to selectively connect individual resistors of the network in different series and/or parallel combinations. Low ohm transistors (not shown) are used in the resistor network to select the desired value of current sense resistance.

When a low noise reference voltage was conventionally required for an oximeter, a high quality reference amplifier having a low noise over a broad frequency range was generally used as a precision reference voltage source. Since the reference voltage acts as a current set point that the feedback type op-amp 11, 21 uses to stabilize a voltage across the current sensing resistor 15, 25, the direct connection of the reference voltage to the op-amp 11, 21 in the present invention places the switch 12, 22 within the feedback loop of op-amp 11, 21 in order to drive the noise from the switch 12, 22. As with conventional systems, the change in diode current sensed by the current sense resistor 15, 25 corresponds to a changing diode current, but since the switching of the reference voltage in the present invention does not create a switching noise, the reference function becomes quicker and more accurate compared with conventional external reference voltage switches. As noted above, the lack of switching noise allows the bandwidth of the reference voltage source to be much smaller, thereby permitting improved low-pass filtering. The noise reduction provided by the present invention significantly lowers 1/f noise of the diode driving circuit, allowing a designer to use improved low-pass filtering while also utilizing a reference voltage source that is much less complex compared with conventional circuits, thereby lowering a cost, power consumption, and complexity of the diode driver circuit. Since a 1/f noise is reduced, a precision reference voltage source in the present invention need only have a low white noise level to provide better low frequency performance compared with costly amplifiers used in conventional reference voltage supplies which require extensive filtering and processing hardware.

The reference voltage, from the reference voltage sources 10, 20 used in the above-described embodiments, provides a clean reference voltage that establishes a current set point for the driver circuit. The reference voltage source 10, 20 includes an extremely low frequency lowpass output filter (not shown). The simple filter makes negligible the aforementioned 1/f noise since the amplitude of the reference voltage is kept at a high level, and the reference noise is reduced by the lowpass filter acting on the high amplitude reference voltage. Switching the reference voltage within the feedback portion of the circuit precludes a need to use extensive filtering while still allowing the filter to eliminate ultra-low frequency noise at small signal levels. Since reducing the LED drive currents by reducing the reference voltage acts to decrease the signal-to-noise (S/N) ratio of the reference voltage, the current set point is preferably adjusted by setting the reference voltage to an optimized value, whereas the actual drive current to the diode 16 is varied by changing the current sensing resistor 15. The current set point acts to regulate the operation of the LED drive circuit, since departure from the set point causes the circuit to operate to reduce the error and restore the intended steady state.

The current being supplied to the diode 17 may be modulated by any combination of appropriate known methods. The current sensed by resistor 15 may be detected and processed for determining, for example, a modulation ratio of a driven red LED signal to a driven infrared LED signal. By then comparing a measured modulation ratio from a photodetector to the driven modulation ratio, an accurate determination of, for example, a phase or pulse width distortion, is used to assist in calibrating the pulse oximeter. In addition, a modulation level for a pulse is selected, for example, in order to minimize perturbation of arterial blood while providing a measurable venous signal. A modulating device (not shown) may be placed in series with the current sensing resistor, or can be used to directly modulate the switch 12, 22 in the feedback loop.

The current through the diode 17 can be actively modulated by, for example, modulating the current being supplied to the diode driver circuit or by modulating the actual switching on and off of the diode. A modulation can be either periodic or non-repetitive. A modulation frequency and decimation rate may be adjusted, for example, in order to minimize the affects of ambient light. Frequency modulation of diode current may include a use of spread spectrum methods. The modulated signal may also be, for example, a pulse width modulated signal or a frequency modulated signal that provides coded data to a photodetector for use in subsequent analysis, although the closed-loop nature of the diode driver should be maintained. The modulation may also include a use of amplitude modulation such as, for example, a modulation of currents through individual diodes. Again, however, any such modulation should be employed without affecting the tightly controlled reference of the closed-loop diode driver. Therefore, time-division multiplexing (TDM) and pulse-width modulation (PWM) are preferably used to modulate the current through the current sensing resistor 15, 25.

An ordinarily skilled artisan would understand that modifications can be made to the invention described herein without departing from the essence and spirit of the invention, which is intended to be defined only by the scope of the claims that follow.

What is claimed is:

1. A pulse oximetry device that converts pulses into light flashes, comprising:
    a diode for emitting the light flashes;
    a current sense element for sensing at least a part of a current being supplied to the diode of the oximeter; and
    a feedback-controlled switch for switching the diode on and off, said feedback controlled switch including an op-amp and a control switch having a first switching state where a first output of the op-amp is used to regulate a current passing through the diode and a second state where said control switch controls an output of said op-amp such that said diode is caused to be switched off.

2. The oximetry device as claimed in claim 1, wherein the diode is an LED.

3. The oximetry device as claimed in claim 1, wherein the diode is a laser diode.

4. The oximetry device as claimed in claim 1, wherein the feedback-controlled switch comprises said op-amp, said control switch, and a transistor.

5. The oximetry device as claimed in claim 4, wherein the op-amp comprises a first input, a second input, and an output, the first input being directly connected to a reference voltage.

6. The oximetry device as claimed in claim 5, wherein the control switch comprises an input, connected to the output of the op-amp, and a plurality of switch outputs.

7. The oximetry device as claimed in claim 6, wherein the transistor comprises a control input, connected to one of the plurality of switch outputs, a current source terminal, and a supply terminal.

8. The oximetry device as claimed in claim 7, wherein the diode is connected to the current source terminal of the transistor.

9. The oximetry device as claimed in claim 8, wherein the supply terminal of the transistor is connected both to the second input of the op-amp and to a second one of the plurality of switch outputs.

10. The oximetry device as claimed in claim 4, wherein the transistor comprises one of a bipolar transistor, a field effect transistor, an insulated-gate semiconductor, and a semiconductor controlled rectifier.

11. A pulse oximeter that converts pulses into light flashes, comprising:
   a plurality of diodes for emitting the light flashes;
   a plurality of current sense elements corresponding to the plurality of diodes, for sensing at least a part of a current being supplied to each respective diode of the oximeter; and
   a feedback-controlled switch for switching a selected one of the plurality of diodes on and off, said feedback controlled switch including an amplifier and a control switch having a first switching state where a first output of the amplifier is used to regulate a current passing through the diode and a second state where said control switch controls an output of said amplifier such that said diode is caused to be switched off.

12. The oximeter as claimed in claim 11, wherein the plurality of diodes are LEDs.

13. The oximeter as claimed in claim 11, wherein the plurality of diodes are laser diodes.

14. The oximeter as claimed in claim 11, wherein the feedback-controlled switch comprises said amplifier, a control switch, and a plurality of transistors corresponding to the plurality of diodes.

15. The oximeter as claimed in claim 14, wherein the amplifier comprises a first input, a second input, and an output, the first input being directly connected to a reference voltage.

16. The oximeter as claimed in claim 15, wherein the control switch comprises a switch input connected to the output of the amplifier, and a plurality of switch outputs corresponding to the plurality of diodes.

17. The oximeter as claimed in claim 16, wherein each of the plurality of transistors comprises a control input, connected to a corresponding different one of the plurality of switch outputs, a current source terminal, and a supply terminal.

18. The oximeter as claimed in claim 17, wherein the each of the plurality of diodes is connected to the current source terminal of a corresponding one of the plurality of transistors.

19. The oximeter as claimed in claim 18, wherein the supply terminal of each of the plurality of transistors is connected both to the second input of the amplifier and to a second one of the plurality of switch outputs.

20. The oximeter as claimed in claim 14, wherein the plurality of transistors comprise one of bipolar transistors, field effect transistors, insulated-gate semiconductors, and semiconductor controlled rectifiers.

21. The oximetry as claimed in claim 1, further comprising a current-changing device for varying a drive current to the diode.

22. The oximetry according to claim 21, wherein the current sensing element comprises a network of individual resistors that are adapted to be selectively connected in different series and/or parallel combinations.

23. The oximetry according to claim 22, further comprising low ohm transistors operative to perform a connecting of ones of the individual resistors.

24. The oximetry according to claim 21, wherein the current sensing element comprises a variable resistor.

25. The oximeter as claimed in claim 11, further comprising a current-changing device for individually varying a plurality of drive currents corresponding to the plurality of diodes.

26. A current driving apparatus in an oximeter, comprising:
   a voltage-to-current converter having a feedback loop between an output loop of the converter and a first input of said converter;
   an unswitched reference voltage source directly connected to a second input of the voltage-to-current converter different than the first input; and
   a switch disposed in the feedback loop,
   whereby the unswitched reference voltage source is isolated from the switch.

27. A method of driving a current through a diode in a pulse oximeter that converts pulses into light flashes, comprising:
   connecting a feedback-controlled device to the diode of the pulse oximeter, the diode being for emitting the light flashes, the feedback-controlled device comprising a feedback loop having a switch;
   switching on and off the diode by changing a switch position of the switch.

28. The method according to claim 27, further comprising changing a value of a current sensing resistor disposed in series with the diode, for changing a drive current to the diode.

29. The method according to claim 28, wherein the changing of the value of current sensing resistor is effected by selectively connecting individual resistors of a resistor network in different series/parallel combinations.

30. The method according to claim 27, further comprising modulating the current through the diode.

31. A method of using a switch for switching current through a light flash emitting diode of a pulse oximeter on or off, the method comprising:
   sensing a current passing through a current path that includes the diode of the pulse oximeter;
   directly connecting a reference voltage to an amplifier;
   causing the amplifier to regulate the current passing through the current path according to the reference voltage and the sensed current; and
   placing the switch in a feedback loop of the amplifier, where the switch switches current through the diode between on and off.

* * * * *